United States Patent
Wagner et al.

(10) Patent No.: US 6,321,608 B1
(45) Date of Patent: Nov. 27, 2001

(54) PASSIVE AEROSOL SAMPLER AND METHODS

(75) Inventors: Jeff Wagner, Oakland, CA (US); David Leith, Chapel Hill, NC (US)

(73) Assignee: The University of North Carolina - Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/544,221

(22) Filed: Apr. 7, 2000

(51) Int. Cl.$^7$ ..................................................... G01N 1/00

(52) U.S. Cl. ......................................................... 73/863.21

(58) Field of Search ..................... 73/28.01, 28.04–28.06, 73/863.21, 863.22, 865.5; 96/413

(56) References Cited

U.S. PATENT DOCUMENTS

| | | |
|---|---|---|
| 4,350,507 | 9/1982 | Greenough et al. . |
| 4,932,254 * | 6/1990 | Davidson et al. .................. 73/28.01 |
| 5,607,497 | 3/1997 | Brown . |
| 5,954,845 | 9/1999 | Willeke et al. . |
| 5,958,111 | 9/1999 | Willeke et al. . |

OTHER PUBLICATIONS

Brown et al., "Preliminary Assessment of a Device for Passive Sampling of Airborne Particulate", *Annals of Occupational Hygiene*, vol. 38, No. 3, pp. 308–318, 1994.

Brown et al., "Field Trials of an Electret–Based Passive Dust Sampler in Metal–Processing Industries", *Annals of Occupational Hygiene*, vol. 39, No. 5, pp. 603–622, 1995.

Brown et al., "A Passive Sampler for Airborne Dust Using an Electret", *J. Aerosol. Sci.*, vol. 23, Suppl. 1, pp. S623–S626, 1992.

Dust Sampling: Button Aerosol Sampler for Inhalable Dust, internet website document found at http://www.skcinc.com/prod/button.html, Dec. 21, 1999, 10:18 a.m.

SKC Passive (Diffusive) Samples, internet website document found at http://www.skcinc.com/passamp.html, Oct. 11, 1999, 2:28 p.m.

Brown et al., "Electret–based Passive Dust Sampler: Sampling of Organic Dusts", *Analyst*, vol. 121, pp. 1241–1246, Sep. 1996.

Vinzents, "A Passive Personal Dust Monitor", *Annals of Occupational Hygiene*, vol. 40, No. 3, pp. 261–28, 1996.

Noll et al., "Characterization of the Deposition of Particles from the Atmosphere onto a Flat Plate", *Atmospheric Environment*, vol. 22, pp. 1461–1468, 1988.

Davies, "Particle–fluid interaction," *Jour. Aerosol Sci.* vol. 10, pp. 477–513, 1979.

CRC *Handbook of Chemistry and Physics*, 77$^{th}$ Ed., CRC Press, Boca Raton, pp. 15–29, 1997.

Stein et al., "The shape of atmospheric particles in Pittsburgh air," *Atmospheric Environment* vol. 3, pp. 443–453, 1969.

Lin et al., "Dry deposition velocities as a function of particle size in the ambient atmosphere," *Aerosol Sci. Technol.* vol. 20, pp. 239–252, 1994.

Hinds, *Aerosol Technology*, John Wiley and Sons, New York, pp. 48, 365, 1982.

(List continued on next page.)

Primary Examiner—Robert Raevis
(74) Attorney, Agent, or Firm—Burns, Doane, Swecker & Mathis, L.L.P.

(57) ABSTRACT

A miniature, passive aerosol particle sampler comprises a scanning electron microscopy mount provided with a collection surface and a removable mesh cover comprising a spacer ring and a mesh sheet. A sampling and analysis method comprises scanning electron microscopy and image analysis to determine a particle-count size distribution. A deposition velocity model comprising a theoretical component and an empirical component is used to determine from the particle-count size distribution the average airborne mass concentration of aerosol particles to which the sampler was exposed.

34 Claims, 7 Drawing Sheets

SIDE VIEW

OTHER PUBLICATIONS

Figures 1A, 1B:
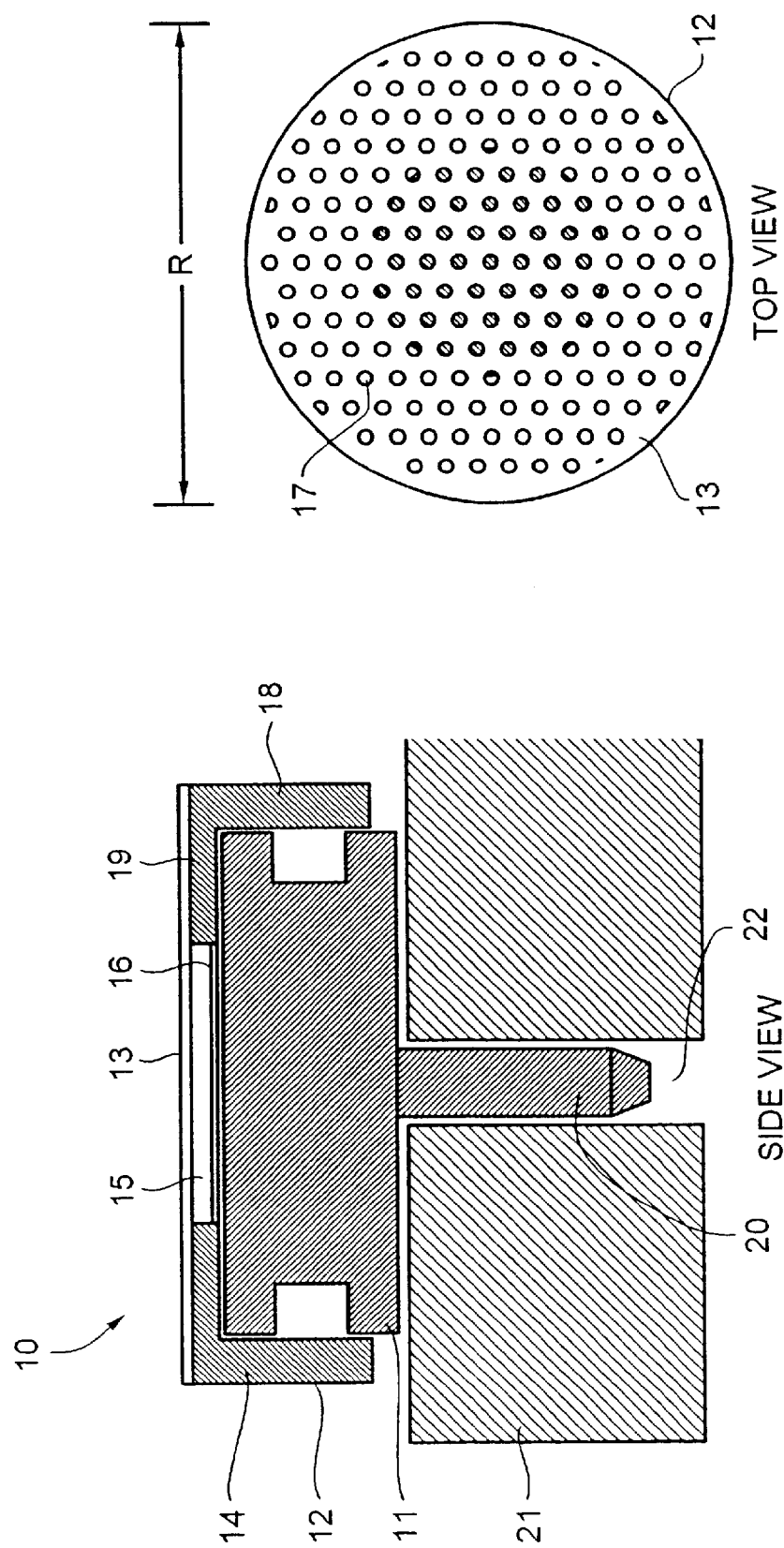

Leith, "Drag on Nonspherical Objects", Aerosol Sci. Technol., vol. 6, pp. 153–161, 1987.

Tohno et al., "Morphological and Dynamic Characterization of Pb Fume Particle Undergoing Brownian Coagulation", *Jourl. Aerosol. Sci.*, vol. 21, pp. 719–732, 1990.

Shimada et al., "Influence of particle inertia on aerosol deposition in a stined turbulent flow field," *J. Aerosol Sci.* vol. 20, pp. 419–429, 1989.

Schneider et al., "A semiempirical model for particle deposition onto facial skin and eyes. Role of air current and electric fields," *J. Aerosol Sci.* vol. 25, pp. 583–593, 1994.

Wood, "A Simple method for the calculation of turbulent deposition to smooth and rough surfaces," *J. Aerosol Sci.* vol. 12, pp. 275–290, 1981.

Sehmel, "Particle deposition from turbulent air flow," *J. Geophys. Res.* vol. 75, pp. 1766–1781, 1970.

Sehmel, "Particle and gas dry deposition: a review", *Atmospheric Environment* vol. 14, pp. 983–1011, 1980.

McRae et al., "Development of a second–generation mathematical model for urban air pollution—I" (*Atmospheric Environment* vol. 16, pp. 679–696, 1982.

H. Schlichting, *Boundary–layer Theory*, $7^{th}$ Ed., McGraw–Hill, New York, p. 603, 1979.

* cited by examiner

TOP VIEW

SIDE VIEW

SIDE VIEW

PASSIVE AEROSOL SAMPLER AND METHODS

At least some aspects of this invention were made with Government support under contract no. P200A40274-96. The Government may have certain rights in this invention.

BACKGROUND OF THE INVENTION

The present invention relates to a miniature, passive device for sampling aerosol particles and dusts. The invention also relates to associated methods for determining the type, size distribution and airborne concentration of particles to which the sampling device was exposed. The device may be deployed as a personal exposure-monitoring device or as a stationary exposure-monitoring device for use in measuring airborne particle hazards.

Aerosol particle samplers (or dust samplers) are devices that may be used to collect airborne particulate matter for subsequent exposure analysis. A goal in aerosol particle sampling is to determine the average airborne mass concentration of particles (mass of particles per unit volume of air) as a function of particle size to which the aerosol sampler was exposed during a sampling period. Typically, such samplers are employed to measure airborne particle hazards for heath-related reasons.

Conventional particle samplers operate by pumping a quantity of the atmosphere containing the particulate matter through the sampler. In one common approach, the particles are collected on a filter and may be assessed by subsequent gravimetric analysis, examination by microscopy, or chemical analysis. Through various calibrations, an assessment of the particles collected with the sampler provides a means for determining an estimate of the average mass concentration of airborne particles to which the sampler was exposed during the sampling period. These types of samplers may be considered active aerosol samplers because the particle-containing atmosphere is drawn into or forced through the sampler by an external pump or vacuum source. Such a sampling device and method are described in U.S. Pat. Nos. 5,954,845 and 5,958,111 issued to Willeke et al.

Aerosol samplers may be either stationary or personal. Stationary samplers are typically used to monitor community exposure in a defined area. However, monitoring community exposure with a few centrally-located aerosol samplers may not adequately monitor exposures in outlying regions. To adequately monitor community exposure in all regions of an area, a large number of samplers may be needed. If active aerosol samplers are being used, the costs involved in providing the necessary pumps and power sources may be substantial. In addition, if long-term exposure monitoring is required, the extended power and maintenance requirements of active samplers can further increase costs.

Personal active samplers are typically smaller than stationary active samplers, but their sampling pumps can be noisy, heavy, or bulky. Further, such samplers require their own power sources, adding to both cost and weight. Considerations of noise, weight and bulk are important because any inconvenience to a person wearing a personal sampler may alter behavior and produce nonrepresentative exposure estimates.

A different approach to aerosol sampling involves the use of passive aerosol samplers which do not operate by drawing or forcing air through the sampler and which do not require sampling pumps. Rather, during sampling, particles passively deposit onto a collection surface by gravity, inertia, diffusion, or through electrostatic interaction if the collection surface is charged. Subsequent analysis of the collected particles is then carried out to determine an estimate of the average mass concentration of airborne particles to which the sampler was exposed during the sampling period.

One type of passive aerosol sampler known in the art is the passive dust sampler described in U.S. Pat. No. 5,607,497 issued to Brown and also described in an article by Brown et al. entitled "Electret-based Passive Dust Sampler: Sampling of Organic Dusts" (*Analyst* Vol. 121, pp. 1241–1246, September 1996). The Brown passive dust sampler collects particles electrostatically with a charged dielectric electret surface. However, calculation of aerosol concentration of particles to which the sampler was exposed requires knowledge of the average aerosol mobility and electret charge, information that is difficult to determine accurately. Alternatively, the electret mass can be correlated with the results of conventional aerosol samplers for different aerosol types. However, the particle sample collected by the Brown et al. sampler is not collected on an electrically conducting surface in a manner convenient for analysis by scanning electron microscopy (SEM).

Another type of passive aerosol sampler is that described by Vinzents in an article entitled "A Passive Personal Dust Monitor" (*Annals of Occupational Hygiene*, Vol. 40, pp 261–28, 1996). The Vinzents passive sampler collects particles onto upward-facing, sideways-facing, and downward-facing sticky substrates. A light extinction measurement technique is used to provide an assessment of the particles deposited on the collection surfaces. However, the Vinzents passive sampler, being approximately 14 cm×6 cm×5 cm in size, is larger and heavier than desired for a personal, passive aerosol sampler. Further, the particle sample collected by the Vinzents sampler is not collected on a collection surface convenient for analysis by SEM.

Accordingly, a need exists for a passive aerosol particle sampler that can be used as a stationary or personal sampling device, that is unobtrusive, that is inexpensive to produce, that provides for convenient SEM analysis, that is easy to use, and that can provide reliable exposure information. The present invention provides a miniature passive aerosol sampler and a passive aerosol sampling and analysis method that achieves these and other goals.

SUMMARY AND OBJECTS OF THE INVENTION

It is an object of the invention to alleviate the deficiencies of the prior art. It is another object of the invention to provide a passive aerosol sampler that provides for convenient SEM analysis and that is easy to use. It is another object of the invention to provide a passive aerosol sampler that provides for convenient analysis by other microscopy techniques including environmental SEM (ESEM), optical microscopy, transmission election microscopy (TEM), and atomic force microscopy (AFM). It is another object of the invention to provide an analysis method for determining an average airborne mass concentration of aerosol particles as a function of particle size from measurements made with the passive aerosol sampler. These and other objects and features of the present invention will be apparent from the written description and drawings presented herein.

In one aspect of the invention there is provided a passive aerosol sampler, comprising:
  a body provided with an electrically conducting collection surface; and
  a removable mesh cover, the removable mesh cover comprising a mesh sheet having a plurality of apertures therein, wherein a first portion of the removable mesh cover is removably attached to the body and a second portion of the removable mesh cover is disposed adjacent to the collection surface, wherein aerosol particles can deposit through the apertures onto the collection surface.

In another aspect of the invention there is provided a method of determining an average airborne concentration of aerosol particles as a function of particle size in a measurement region from a sample of aerosol particles collected on a collection surface of a passive aerosol sampler, the passive aerosol sampler having a body provided with the collection surface and a removable mesh cover removably attached to the body, the removable mesh cover having a plurality of apertures therein, comprising the steps of:

carrying out microscopy on the sample of aerosol particles collected on the collection surface;

obtaining images of the sample of aerosol particles using said microscopy;

determining a particle-count size distribution using image analysis of the images; and calculating the average airborne concentration of aerosol particles as a function of particle size from the particle-count size distribution using a mathematical model having a theoretical component and an empirical component, wherein the empirical component is related to the geometrical characteristics of the mesh cover.

The foregoing has been provided as a convenient summary of aspects of the invention. The invention intended to be protected is, however, defined by the claims and equivalents thereof.

BRIEF DESCRIPTION OF THE DRAWINGS

FIG. 1*a* is an illustration of a first embodiment of the passive aerosol sampler according to the present invention in partial cross section configured with a scanning electron microscopy sample mount.

FIG. 1*b* is a plan-view illustration of the passive aerosol sampler shown in FIG. 1*a.*

FIG. 2 is a magnified cross-sectional view of the passive aerosol sampler shown in FIG. 1*a* illustrating the deposition of particles through the mesh onto the collection surface.

FIG. 3*a* is a cross-sectional illustration of a passive aerosol sampler according to the present invention configured for personal exposure monitoring.

FIG. 3*b* is a perspective view of the passive aerosol sampler illustrated in FIG. 3*a.*

FIG. 4 is a cross-sectional illustration of a passive aerosol sampler according to the present invention configured for stationary exposure monitoring.

FIG. 5 is a schematic illustration in perspective view of a wind tunnel useful for sampler calibration.

FIG. 6 is a cross-sectional illustration of an embodiment of a passive aerosol sampler according to the present invention configured with a transmission electron microscopy grid for collecting aerosol particles.

FIG. 7 is a cross-sectional illustration of an embodiment of a passive aerosol sampler according to the present invention configured with an atomic force microscopy sample mount.

DETAILED DESCRIPTION OF THE PREFERRED EMBODIMENTS OF THE INVENTION

The disclosed embodiments address the need for a convenient and inexpensive passive aerosol sampler for collecting airborne particles in exposure monitoring. The embodiments also address the need for a sampling and analysis method that is easy to implement and that provides reliable exposure information.

In the description that follows, the preferred embodiments of the passive aerosol sampler according to the present invention are first described. The use of the inventive passive aerosol sampler in aerosol particle sampling and methods of data analysis to determine particle exposure are then described. The associated methods of sampler calibration are then described. Finally, alternative embodiments of the passive aerosol sampler and associated methods are described.

I. PASSIVE AEROSOL SAMPLER

A preferred embodiment of the miniature, passive aerosol sampler 10 according to the present invention is illustrated in FIG. 1*a* in partial cross section. The passive sampler is about the size of a dime and is designed to be small, lightweight, sturdy, convenient for microscopy analysis, and resistant to sample contamination and resuspension. A body 11 of the sampler is composed of either an aluminum or carbon scanning electron microscopy (SEM) sample mount having a protruding post 20 that fits into a mounting hole 22 of a holder 21 (partially shown). Samplers with bodies 11 formed of aluminum are preferable for size distribution analyses because their high conductivity allows for good resolution. Samplers with bodies 11 formed of carbon are preferable when elemental x-ray analysis is important to minimize interference of x-rays from the sampler body 11 with the elemental x-ray spectra of the collected particles.

As illustrated in partial cross section in FIG. 1*a*, a circular removable mesh cover 12 is disposed on the body 11 and comprises a mesh sheet 13 securely bonded to a circumferential spacer ring 14. The spacer ring 14 has a side portion 18 and a top portion 19 with a central, circular opening. The spacer ring 14 and the mesh sheet 13 are preferably formed from stainless steel, but other metals or alloys may also be used. The removable mesh cover 12 is mounted onto the body 11 with an adhesive suitable for use in SEM applied between the upper surface of the body 11 and the circumferential spacer ring 14. For example, spray-mount adhesive can be sprayed onto the upper surface of the body 11 while masking the central portion of the upper surface of the body 11 to prevent coating the central portion with adhesive. The removable mesh cover 12 is pressed into contact with the body 11. The spray adhesive securely fastens the removable mesh cover 12 during sampling, but allows removal of the cap 12 afterward for analysis by SEM.

A semi-quiescent collection region 15 is formed between the mesh sheet 13 and a circular collection surface 16 disposed at a central portion of the upper surface of the body 11 (SEM sample mount). Because the manufacturing of SEM sample mounts often creates microscopic grooves and imperfections in the machined surfaces, the collection surface 16 can be provided by a circular piece of smooth, aluminum adhesive tape suitable for SEM use mounted at the base of the collection region 15 prior to installation of the removable mesh cover 12. The particles collected on the smooth collection surface 16 can then be analyzed by SEM with minimal interference by extraneous surface imperfections.

Though the passive aerosol sampler illustrated in FIGS. 1*a* and 1*b* has a removable mesh cover 12 comprising a mesh sheet 13 securely bonded to a circumferential spacer ring 14, those skilled in the art will recognize that the removable mesh cover 12 could be configured in a variety of ways. Generally, the removable mesh cover comprises a mesh sheet having a plurality of apertures therein and is configured such that a first portion of the removable mesh cover, such as a circumferential portion, is removably attached to the body of the sampler. Further, the removable mesh cover is generally configured such that a second portion of the removable mesh cover, such as a central portion, is disposed adjacent to the collection surface, wherein aerosol particles can deposit through the apertures onto the collection surface.

Though the body 11 illustrated in FIG. 1a has a protruding post 20, a conventional SEM sample mount substantially similar to that shown in FIG. 1a but having a threaded hole rather than a protruding post may also be used for the body 11. In this instance, the holder 21 should possess a protruding threaded screw upon which body 11 is secured. Further, if a body 11 is provided with a threaded hole rather than a protruding post, atomic force microscopy (AFM) as well as SEM may be directly carried out on the sample of collected particles as deposited on the collection surface. If AFM is to be utilized in this manner, the height of the body 11 should not exceed the height of the sample observation region of the AFM. Conventional SEM sample mounts ranging from about 5 mm to 10 mm in height having threaded holes will typically satisfy this requirement. An alternative embodiment of the passive aerosol sampler configured using an AFM sample mount is later described in more detail.

As illustrated in FIG. 1b, the removable mesh cover 12 has a diameter R. The diameter of the removable mesh cover 12 is determined by the diameter of the body 11 over which the cap 12 fits as illustrated in FIG. 1a. SEM sample mounts of a variety of sizes may be used for the body 11, and the diameter of the removable mesh cover 12 will vary accordingly. Preferably, the diameter of the body 11 ranges from about 10 mm to 33 mm. Most preferably, the diameter of the body 11 ranges from about 10 mm to 15 mm. Preferably, the diameter of the removable mesh cover 12 ranges from about 12 mm to 38 mm. Most preferably, the diameter of the removable mesh cover 12 ranges from about 12 mm to 18 mm. Determination of particular diameters for the body 11 and the removable mesh cover 12 is within the purview of one skilled in the art. It has been found that a removable mesh cover 12 with a diameter of 15 mm provides an advantageous size for use in conjunction with a body 11 12.7 mm in diameter.

The collection region 15 and the collection surface 16 may be configured in a variety of shapes and sizes. A circular collection surface 16 disposed at the base of a circular collection region 15 as illustrated in FIGS. 1a and 1b is preferred. Preferably, the diameter of the collection surface 16 and collection region 15 ranges from about 5 mm to 17 mm. Most preferably, the diameter of the collection surface 16 and the collection region 15 ranges from about 5 mm to 8 mm. In addition, the height of the collection region 15 preferably ranges from about 1 mm to 3 mm. Most preferably, the height of the collection region ranges from about 1 mm to 1.5 mm. It has been found that a spacer ring 14 configured to provide a circular collection region 15 about 1.2 mm deep and about 7 mm in diameter is advantageous.

As further illustrated in FIG. 1b, the mesh sheet 13 comprises an array of apertures 17 arranged in a predetermined pattern. A purpose of the mesh sheet 13 is to prevent deposition of very large particles, such as sand, hair, or other debris onto the collection surface 16. The particle sizes that are excluded by the mesh are determined by the mesh aperture size. A smaller aperture size is desirable to prevent unwanted large particles from depositing onto the collection surface 16. However, a mesh with a large number of smaller apertures may have a tendency to collect a greater number of particles on the mesh itself by diffusion and interception, potentially reducing the number of particles collected during sampling. Mesh sheets 13 with a variety of aperture configurations and sizes as noted below may be utilized to balance these two concerns.

Figure 2:
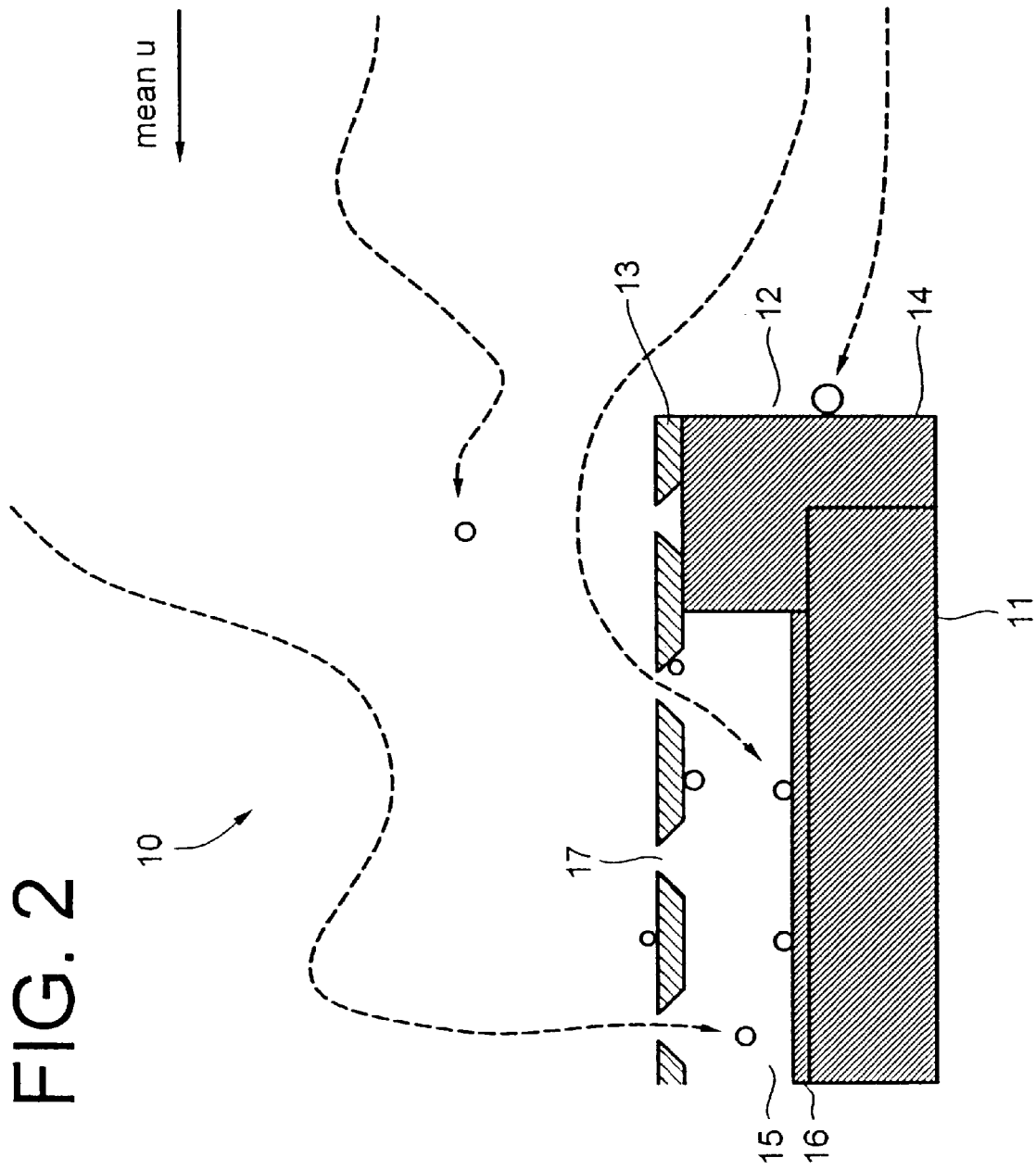

Mesh sheets 13 having a variety of aperture arrangements and shapes may be utilized. A particular example of an advantageous mesh sheet 13 is illustrated in FIG. 1b in plan view and in FIG. 2 in cross section. The mesh sheet 13 illustrated in FIG. 1b has circular apertures 17 arranged in a triangular-lattice pattern. In addition, as illustrated in FIG. 2, the apertures 17 may be configured with a conical cross section. If a mesh sheet 13 having apertures of conical cross is used, it is preferable for the smaller openings to be disposed at the upper surface of the mesh sheet as illustrated in FIG. 2. Alternatively, the mesh sheet 13 may possess apertures 17 arranged in other types of patterns, and the apertures 17 may be configured with openings in shapes other than circles.

In addition, mesh sheets 13 having a range of aperture sizes and a range of thicknesses may be utilized. The aperture size may be advantageously chosen to exclude particles of a predetermined maximum diameter based upon anticipated sampling conditions. Preferably, the aperture diameter ranges from about 75 $\mu$m to 610 $\mu$m. Preferably, the mesh thickness ranges from about 50 $\mu$m to 380 $\mu$m. Most preferably, the mesh thickness ranges from about 50 $\mu$m to 200 $\mu$m.

In addition, mesh sheets 13 having a range of percent open areas may be utilized. It may be desirable to provide a mesh sheet 13 with a relatively small percent open area for sampling aerosol particles in extremely dusty conditions to prevent overdeposition of particles on the collection surface 16. Conversely, it may be desirable to provide a mesh sheet 13 with a relatively large percent open area to enhance the collection of particles under conditions where a low concentration of airborne particles is anticipated. Preferably, the percent open area ranges from about 9% to 38%. Most preferably, the percent open area ranges from about 20% to 38%.

Mesh sheets may be advantageously formed from commercially available mesh materials. For example, a mesh material such as that illustrated in FIGS. 1b and 2 having a thickness of 127 $\mu$m, a percent open area of about 27%, and apertures of conical cross section (top diameter of 160 $\mu$m; bottom diameter of 225 $\mu$m) with a center-to-center spacing of about 280 $\mu$m is commercially available from Buckbee-Mears, St. Paul, Inc.

Prior to assembly and sampling, the components of the passive aerosol sampler 10 are thoroughly cleaned and protected from contamination. A preferred cleaning method involves washing the body 11, the removable mesh cover 12, and a circular section of aluminum adhesive tape (if utilized) with conventional laboratory soap, followed by rinsing in deionized water. The components are then rinsed in an appropriate solvent such as methanol and the parts are then dried with blasts of nitrogen gas or filtered, compressed air. The mesh sheet 13 may be further cleaned with a fine-haired brush and additional blasts of nitrogen gas or filtered, compressed air to clear the apertures 17 of any debris. A conventional plastic SEM sample-mount case, such as available from Ted Pella, Inc., having one or more pedestals with holes to securely grip the post 20 of the body 11, is also cleaned using the above-mentioned method. The body 11 and the removable mesh cover 12 are then assembled as described above and securely placed in the plastic SEM sample-mount case until deployed for sampling, at which time the body 11 is placed in the holder 21 as described above.

The deposition of particles onto the collection surface 16 during sampling is illustrated in FIG. 2. As shown in FIG. 2, particles travel from the atmosphere near the surface of the mesh sheet 13, through the apertures 17, into the collection region 15, and finally onto the collection surface 16. In addition, particles may also be captured on the surfaces of the mesh sheet 13 itself as illustrated in FIG. 2.

It may be desirable to maintain a library of passive aerosol samplers with different mesh characteristics suited for different sampling conditions. Samplers having different mesh characteristics will possess different calibration factors (described below) to provide reliable measurements of aerosol particle exposure under various conditions.

An advantage of the passive aerosol sampler 10 described above and illustrated in FIGS. 1 and 2 is that the sampler body 11 is conveniently formed from a conventional SEM sample mount. Therefore, the collected particle sample may be easily examined by SEM after removing the removable mesh cover 12 from the sampler 10 without disturbing the collected particle sample. Analysis by SEM further provides the advantage of utilizing energy-dispersive x-ray fluorescence (EDXRF) to determine the chemical constituents of the collected particles. In addition, if it is anticipated that the collected particle sample may contain volatile constituents, the collected particle sample may be examined by environmental SEM, a technique that is not carried out in high vacuum as is conventional SEM.

Figure 3A:
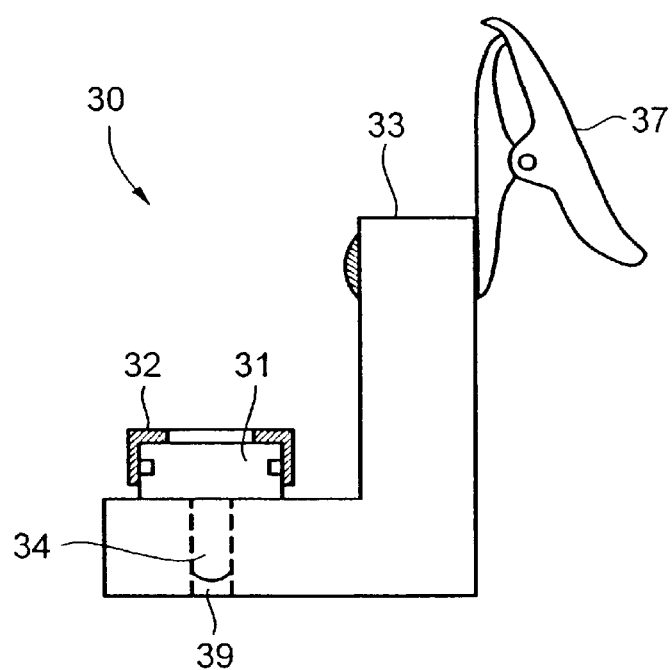

As noted previously, the passive aerosol sampler may be deployed for personal exposure monitoring or for stationary exposure monitoring. An embodiment for personal exposure monitoring is schematically illustrated in cross section in FIG. 3a. As shown in FIG. 3a, a sampler 30 for personal exposure monitoring comprises a body 31 and a removable mesh cover 32. The body 31 and the removable mesh cover 32 are like those shown previously in FIG. 1a. A post 34 protrudes from the body 31 and fits into a mounting hole 39 of an L-shaped holder 33. Preferably, the holder 33 is made of a plastic material, and the mounting hole 39 is sized such that the post 34 fits snugly into the mounting hole 39. In this manner the body 31 is held securely in place in the holder 33. The sampler 30 further comprises a clip 37 attached to the holder 33, allowing the sampler to be clipped to the collar or elsewhere near the upper torso of a person for whom exposure is being monitored.

Figure 4:
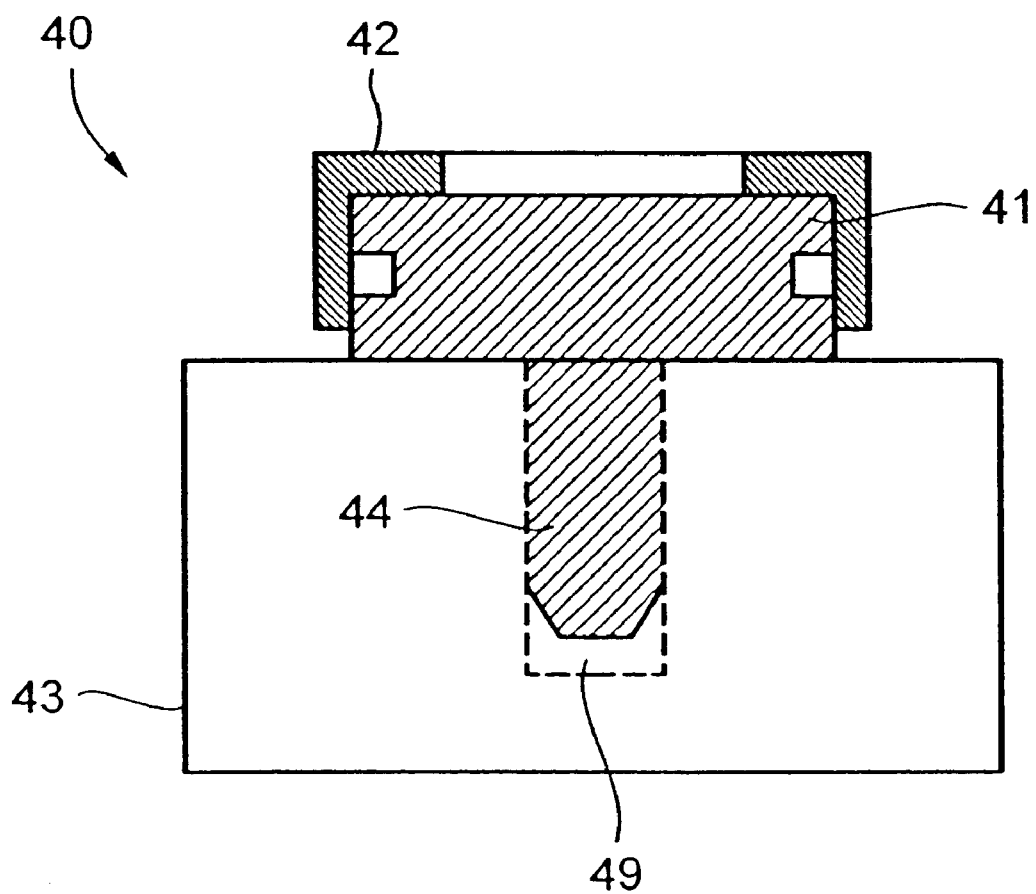

An embodiment of the sampler configured for stationary exposure monitoring is schematically illustrated in cross section in FIG. 4. As shown in FIG. 4, a sampler 40 for stationary exposure monitoring comprises a body 41 and a removable mesh cover 42 like those shown previously in FIG. 1a. A post 44 protrudes from the body 41 and fits into a mounting hole 49 of a holder 43. Though the holder 43 is shown in the shape of a rectangular block, the holder 43 may be provided in a variety of shapes. Preferably, the holder 43 is made of metal or plastic. If the holder 43 is made of plastic, it is desirable that the size of the hole 49 be configured to provide a snug fit around the post 44. Holders of this type are conventionally available in standard SEM sample storage boxes such as available from Ted Pella, Inc.

Prior to sampling, whether for personal exposure monitoring or for stationary exposure monitoring, the sampler body and removable mesh cover are provided thoroughly precleaned in a clean SEM sample-mount case as noted above. Alternatively, the sampler already placed in the holder may be provided in an appropriate clean plastic case or a resealable plastic bag. In personal exposure monitoring, the sampler 30 is then removed from the container and clipped to the person for whom exposure is being monitored for the duration of the sampling period. In stationary exposure monitoring, the sampler 40 is removed from the container and placed in an appropriate location for the duration of the sampling period. In either instance, the container is closed or resealed to prevent contamination of the inner surfaces of the container. After sampling, the sampler is returned to the container. The container and the sampler therein are then returned to the laboratory for subsequent analysis by SEM or other microscopy.

II. DETERMINING AIRBORNE PARTICLE CONCENTRATIONS

A. Approach

As noted above, in passive aerosol sampling it is desired to determine the average airborne mass concentration of particles (mass of particles per unit volume of air) to which the sampler was exposed during a sampling period. It is particularly desirable to determine this quantity as a function of particle size. Various standard measures of the average mass concentration of particles are known in the art and may be determined by integrating the average mass concentration of particles over a particle-size range of interest, typically up to some particular particle size. For example, the quantity PM2.5 is known in the art as the average airborne mass concentration of particles with sizes up to an aerodynamic diameter of 2.5 micrometers. Similarly, PM10 is known in the art as the total airborne mass concentration of particles with sizes up to an aerodynamic diameter of 10 micrometers.

It is known in the art that the average mass concentration of airborne particles as a function of the particle size may be determined from a measurement of the flux of particles deposited on a smooth collection surface according to the following equation:

$$C = F/v_{dep} \qquad (1)$$

where C is the average mass concentration of airborne particles, F is the mass flux of particles (mass of particles per unit area per unit time) deposited on the collection surface during a given time period, and $v_{dep}$ is a mathematical expression for the deposition velocity of particles deposited on the collection surface. F is also referred to as the mass flux distribution. All three quantities are functions of particle size and are most conveniently expressed as functions of the particle aerodynamic diameter, $d_a$, known to those skilled in the art. The aerodynamic diameter is the diameter of a unit density sphere with the same settling velocity as that of the particle.

Generally, the determination of C in passive aerosol particle sampling involves experimentally measuring the quantity F by analyzing particles collected with a passive aerosol sampler, choosing or calculating an appropriate expression for $v_{dep}$, and calculating C from these expressions. Various models, known as deposition velocity models, are known in the art that provide expressions for $v_{dep}$ as described in more detail below. Conventionally, the expressions for $v_{dep}$ known in the prior art apply to the deposition of particles onto smooth, unobstructed collection surfaces.

Conventional expressions for $v_{dep}$, however, are insufficient to adequately provide a determination of C from F using Equation 1 for the passive aerosol sampler according to the present invention because the geometrical characteristics of the mesh sheet of the inventive passive aerosol sampler affect the deposition of particles onto the collection surface. A different approach for determining C from F that accounts for the influence of the geometrical characteristics of the mesh sheet has been developed according to the present invention.

In the inventive method presented here, an overall deposition velocity is divided into two components. The first is an ambient deposition velocity, $v_{amb}$, which describes the deposition velocity a particle would normally have when depositing onto a flat, smooth surface. This component is expressed as a mechanistic equation. The second component is the "mesh factor," $\gamma_m$, an empirical correction which is intended to account for the effects of the geometrical characteristics of the mesh, that is, the size, shape, configuration and open area of the apertures as discussed above. This overall deposition velocity is then expressed as $$v_{dep} = v_{amb} \gamma_m. \tag{2}$$

With this inventive approach, an equation analogous to Equation 1 can be written as $$C = F/(v_{amb} \gamma_m). \tag{3}$$

In order to determine C from a measurement of F, expressions for $v_{amb}$ and $\gamma_m$ must first be known. The expression for $v_{amb}$ is obtained using a procedure generally known in the art for calculating deposition velocities as described in more detail below. Once $v_{amb}$ is calculated, a semi-empirical expression for $\gamma_m$ is determined by measuring F for a known aerosol with a known airborne mass concentration of particles, C. Such a calibration process may be carried out in a wind tunnel as described in more detail below. With known expressions for $v_{amb}$ and $\gamma_m$, C for an unknown aerosol under actual sampling conditions may then be determined from a measurement of F. These various steps are now described.

B. Determination of the Mass Flux Distribution, F

The mass flux distribution (mass of particles collected per unit area per unit time as a function of particle size) is proportional to the particle-count size distribution (number of particles collected as a function of size), which is the quantity directly measured from images of the collected sample of aerosol particles. The procedure for determining the particle-count size distribution from a collected sample of aerosol particles is now described.

After a sample of aerosol particles has been collected with the passive aerosol sampler, the sampler is transported to the laboratory in a protective container such as described above. In the laboratory, the container is opened, the passive aerosol sampler is removed, the sampler body (SEM mount) is removed from the holder, and removable mesh cover is removed from the sampler body. The particles collected on the collection surface are then analyzed using one or more microscopy techniques. Analysis by SEM is the preferred technique and may carried out, for example, with a SEM such as a Cambridge S-200 SEM (Leo Inc., Fornwood, N.Y.).

Before obtaining SEM images, it is preferable to sputter-coat the body of the passive sampler with a thin metal film of gold or a 60/40% gold/palladium alloy to enhance sample conductivity and resolution. A coating 3 nm to 5 nm thick is generally sufficient to provide adequate conductivity to minimize sample charging, but thicknesses of up to 10 nm to 20 nm may be used to further increase conductivity if the anticipated particle sizes are larger than 1 μm in diameter.

The body of the sampler may then be placed in a SEM for analysis. In addition to providing SEM images, the SEM analysis may include characterization of the particle sample by energy dispersive x-ray fluorescence (EDXRF) to determine the chemical constituents of the collected particles.

To measure the particle-count size distribution of the collected particles, SEM images of the collection surface containing the collected particles are first obtained. Multiple microscope images are taken across the collection surface in a random manner, and the images are further taken at several different magnifications. Magnifications of 250–12,000× are preferred for sizing 0.1–10 μm particles. The images may be obtained in photographic format and subsequently digitized, or the images may be acquired in digitized format directly if the SEM is equipped with computerized capability. The images are then analyzed using a computer with image analysis software to count the particles and to measure their projected areas. An image acquisition system such as Spectral Engine 4.0 (4Pi Analysis Inc., Durham, N.C.) and image analysis software such as SigmaScanPro (Jandel Scientific, San Rafael, Calif.) are useful for these purposes.

A decision rule is used to count and size particles that are only partially within a given SEM field. Borders of width W, corresponding to the largest particle size expected to be present, are applied to the bottom and right sides of each SEM field. All particles touching these two borders are sized, while all particles touching the other two sides are not. The maximum-measurable particle size is then equal to W. At the highest magnifications, W should not be allowed to exceed a certain measure of the field height. It has been found that restricting W to ⅛ of the field height is preferred, but other criteria may chosen. In addition, a minimum-measurable particle size is set for all magnifications to prevent inaccurate sizing of small particles. It has been found that a minimum measurable particle size of 7 pixels is preferred, but other sizes may be chosen.

After the projected areas of the particles are measured, those projected areas are converted into projected-area diameters, $d_{pa}$, determined by equating the measured projected area of each particle to that of a sphere with the same projected area. In other words, $d_{pa}$ is given by $$\text{measured projected particle area} = \frac{\pi}{4}(d_{pa})^2 \quad (4)$$

Using Equation 4, a $d_{pa}$ value may be determined for each counted particle.

Because particles are typically not spherical, it is desirable to express the particle-count size distribution in terms of a different measure of the particle size other than $d_{pa}$. The most common and convenient measure of particle size for this purpose is the aerodynamic diameter, $d_a$, as noted above. Other measures of particle size are also useful and include the equivalent-surface diameter, $d_{es}$, which is the diameter of a sphere with the same surface area as the particle and the equivalent-volume diameter, $d_{ev}$, which is the diameter of a sphere with the same volume as the particle. It is desirable to convert the $d_{pa}$ value for each particle into corresponding $d_{es}$, $d_{ev}$, and $d_a$ values for use in various expressions using conversion equations known in the art as described below.

After converting the $d_{pa}$ values into $d_{es}$, $d_{ev}$, and $d_a$ values, a particle-count size distribution for the collected particles is then generated by specifying particle-size bins of appropriate width in terms of $d_a$ for all identified particles and by counting the number of particles corresponding to each bin. Though the particle-count size distribution is expressed in terms of $d_a$, each particle in a given bin also has an associated $d_{es}$ value and an associated $d_{ev}$ value.

The expressions for converting the $d_{pa}$ values into $d_{es}$, $d_{ev}$, and $d_a$ values are given by $$d_{es} = d_{pa}\left(\frac{f}{\pi}\right)^{1/2} \quad (5)$$

$$d_{ev} = \frac{d_{pa}}{S_v} \quad (6)$$

$$d_a = d_{ev}\left(\frac{\rho_p C_{c,dev}}{\rho_0 C_{c,da}}\frac{1}{S_d}\right)^{1/2} \quad (7)$$

where f is the surface shape factor, $S_v$ is the volume shape factor, $S_d$ is the dynamic shape factor, $\rho_p$ is the density of the particulate material, and $\rho_o$ is the unit particle density. Equations 6 and 7 can be combined to give $$\frac{d_a}{d_{pa}} = \left(\frac{C_{c,dev}}{C_{c,da}}\right)^{1/2}\left(\frac{\rho_p}{\rho_0}\frac{1}{S_d}\right)^{1/2}\frac{1}{S_v} \quad (8)$$

where $C_{c,dev}$ and $C_{c,da}$ are the Cunningham correction factors which are given by $$C_{c,dev} = 1 + \left(\frac{2L}{d_{ev}}\right)\left(1.257 + 0.4e^{-\left(\frac{1.1 d_{ev}}{2L}\right)}\right) \quad (9)$$

$$C_{c,da} = 1 + \left(\frac{2L}{d_a}\right)\left(1.257 + 0.4e^{-\left(\frac{1.1 d_a}{2L}\right)}\right). \quad (10)$$

In the expressions for $C_{c,dev}$ and $C_{c,da}$ above, L is the mean free path for air, which is approximately $6.5 \times 10^{-8}$ meters at 25° C. Note that for particle sizes>1 μm, $C_c$ approaches 1, and $d_a/d_{pa}$ in Equation 8 does not vary with particle size.

Published data reproduced in Table 1 can be used to estimate F, $S_v$, $S_d$ and $\rho_p$ for use in the conversion expressions for $d_{es}$, $d_{ev}$ and $d_a$ in Equations 5–7. Except where indicated, all tabulated values in Table 1 are either measured quantities or are derived from measured quantities. To use Table 1 most effectively, one should have some knowledge of the aerosol sample's identity. This information can be obtained from the microscopy and x-ray fluorescence. In some cases, the aerosol's composition may be homogenous or well specified, such as when sampling in certain industrial environments. In many cases, however, average parameter values must be assumed for a fairly heterogeneous aerosol. For example, a value of $\rho_p=2.0$ g/cm³ may be selected as an average particle density value when sampling urban atmospheric aerosols as noted in an article by Noll et al. entitled "Characterization of the deposition of particles from the atmosphere onto a flat plate" (*Atmospheric Environment*, Vol. 22, pp. 1461–1468, 1988).

Various approaches for estimating f, $S_v$, $S_d$ and $\rho_p$ are known to those skilled in the art, and Table 1 is meant to be illustrative rather than exhaustive. Once average aerosol types have been identified, Table 1 may be consulted to obtain f, $S_v$, and $S_d$. For particle types with no $S_v$ or $S_d$ values listed in Table 1, $d_a$ may be calculated directly using the tabulated $d_a/d_{pa}$ values in Table 1. The $d_a/d_{pa}$ values in Table 1 are not size-dependent and are only valid for particle sizes greater than 1 μm. For particles smaller than 1 μm, the tabulated $d_a/d_{pa}$ values are

TABLE 1

Shape factors and densities for various particle types

| Particle type | Ref. | $\rho_p$ (g/cm³) | $S_v$ | $S_d$ | f | $d_a/d_{pa}$[a] |
|---|---|---|---|---|---|---|
| Common dusts | | | | | | |
| Quartz | D | 2.65 | 1.2–1.4 | 1.36 | 2.4 | 0.97–1.16 |
| Sand | D | 2.5 | 1.3 | 1.57 | 2.95 | 1.0 |
| China clay | D | 2.2 | — | — | — | 0.92 |
| Talc | D | 2.6 | 1.5 | 2.04 | 2.18 | 0.73–0.77 |
| Anthracite coal | D | 1.5 | 1.5 | 1.37 | 2.2 | 0.70 |
| Bituminous coal | D | 1.4 | 1.3 | 1.05–1.11 | 3.02 | 0.87–0.90 |
| Glass | D | 2.6 | — | — | — | 1.08–1.34 |
| Cotton | D | 1.5 | — | — | — | 0.72–0.78 |
| Limestone (CaCO₃) | C/D | 2.7 | 1.5 | — | — | — |
| Gypsum (CaSO₄2H₂O) | C/D | 2.3 | 1.6 | — | — | — |
| Heterogeneous aerosols | | | | | | |
| 1969 Pittsburgh aerosol | S | 2.2 | — | — | — | 0.68 |
| 1986 Chicago aerosol | N | 2.0[b] | 1.89 | 1.41[b] | — | 0.63[c] |
| 1992 Chicago aerosol | L | 1.77 (fine)[b] 2.64 (coarse)[b] | 1.61 | 1.41[b] | — | 0.74[c] |
| General shapes | | | | | | |
| Sphere | H | [1.0] | 1.00 | 1.00 | 3.14 | 1.00 |
| Cube | H | [1.0] | 1.11 | 1.02 | — | 0.89 |
| Compact flake | D | — | — | 1.34 | — | 2.38 | — |

[a]For $d_p$ < 1 μm, multiply value by ($C_{cdev}/C_{cda}$).
[b]Estimated, not measured.
[c]Calculated using estimated parameter.
D = Davies, "Particle-fluid interaction," Jour. Aerosol Sci. Vol 10, pp. 477–513 (1979).
C = CRC Handbook of Chemistry and Physics, 77th Ed., CRC Press, Boca Raton, pp. 15–29 (1997).
S = Stein et al., "The shape of atmospheric particles in Pittsburgh air," Atmospheric Environment Vol. 3, pp. 443–453 (1969).
N = Noll et al., "Characterization of the deposition of particles from the atmosphere to a flat plate," Atmospheric Environment Vol. 22, pp. 1461–1468 (1988).
L = Lin et al., "Dry deposition velocities as a function of particle size in the ambient atmosphere," Aerosol Sci. Technol. Vol. 20, pp. 239–252 (1994).
H = Hinds, Aerosol Technology, John Wiley and Sons, New York, pp. 48, 365 (1982).

multiplied by ($C_{c,dev}/C_{c,da}$). However, an estimate of $S_v$ is still required to determine $d_{ev}$ from $d_a$ as given by Equation 6 for use in determining the mass flux size distribution as described below.

To estimate the shape factors $S_v$ and $S_d$ whose values are not listed in Table 1, the average shape of the collected particles (i.e., flaky, angular, or rod-like) should be determined by microscopy. Then, $S_d$ and $S_v$ may be estimated using tabulated values for various particle shapes. Parameters for only the most basic shapes are given in Table 1. Parameters for other shapes are provided in the published literature known in the art such as the article by Davies entitled "Particle-fluid interaction" (*Jour Aerosol Sci.*, Vol. 10, pp. 477–513, 1979) and the book by Hinds entitled *Aerosol Technology* (John Wiley and Sons, New York, pp. 48, 365, 1982). In addition, procedures exist known to those in the art for calculating $S_d$ for a given geometric shape as described, for example, in the article by Leith entitled "Drag on nonspherical objects" (Aerosol Sci. Technol., Vol. 6, pp. 153–161, 1987) and in the article by Tohno et al. entitled "Morphological and dynamic characterization of Pb Fume particle undergoing Brownian coagulation" (*Jour. Aerosol Sci.*, Vol. 21, pp. 719–732, 1990).

After counting the particles, measuring their projected areas, calculating their associated $d_{pa}$ values, and converting the $d_{pa}$ values into $d_{es}$, $d_{ev}$, and $d_a$ values, the particle-count size distribution may be formed as noted above by specifying the number and width of the size bins and by counting the number of particles corresponding to each bin in terms of $d_a$. Though the particle-count size distribution is most conveniently expressed as a function of, $d_a$, other size variables may be used. Further, the number and width of size bins is arbitrary. For comparison with results from another sampler, such as a reference sampler, size bins that match those of the other sampler may be used.

The particle-count size distribution is then converted to a mass flux size distribution. The average mass flux (mass per unit area per unit time) for bin i is given by $$F_i = \frac{\pi N_i (\overline{d}_{ev})_i^3 \rho_p}{6 A_i t} \quad (11)$$

where $N_i$ is the number of particles counted in size bin i, $\rho_p$ is the density of the material making up the particles, and t is the sampling time. The total field area used for counting, $A_i$, varies with particle size because for any given magnification, some size bins will not be within measurement limits. For these size bins, the magnification's field area is not counted. The equivalent-volume diameter, $d_{ev}$ is the diameter of a sphere with the same volume as the particle as noted above. The $3^{rd}$-moment-average of the equivalent volume particle diameter, $\overline{d}_{ev}$, can be used in calculating average mass flux of the size bin from the measured particle sizes and is given by:

$$\overline{d}_{ev} = \left[ \frac{(d_{ev})_{i,h}^4 - (d_{ev})_{i,L}^4}{4((d_{ev})_{i,h} - (d_{ev})_{i,L})} \right]^{\frac{1}{3}} \quad (12)$$

where $(d_{ev})_{i,L}$ and $(d_{ev})_{i,h}$ are $d_{ev}$ values corresponding to the lower and upper $d_a$ limits of size bin i. It is appropriate to use $d_{ev}$ in calculating the average mass flux of the size bin because $d_{ev}$ is the relevant physical parameter to provide a measure of particle volume. However, as noted above, $F_i$ and $N_i$ are still most conveniently expressed in terms of aerodynamic diameter, $d_a$. The combination of $F_i$ for the various bins provides the mass flux size distribution F.

C. Calculation of $v_{amb}$

It is known in the art that conventional particle deposition onto a smooth, horizontal surface due to turbulent forces and gravity may be described by the steady-state equation $$F = C v_{dep-c} = (D + D_e) \frac{dc}{dy} + v_t c. \quad (13)$$

In Equation 13, $v_{dep-c}$ is a conventional deposition velocity, F is the mass flux of particles deposited onto the surface as a function of particle diameter, C is the ambient particle mass concentration, D is the Brownian diffusion coefficient (D=kTC$_c$/3π $\mu d_{es}$), k is the Boltzmann constant, T is the ambient temperature, $C_c$ is the Cunningham correction factor, $\mu$ is the dynamic viscosity, $D_e$ is the turbulent eddy diffusion coefficient, c is the particle mass concentration at height y above the surface, $v_t$ is the terminal settling velocity ($v_t$=τg), τ=($\rho_0 d_a^2 C_c$)/(18$\mu$), $\rho_0$ is the unit particle density, and g is the gravitational acceleration. The equivalent-surface diameter, $d_{es}$, is the diameter of a sphere with the same surface area as the particle, and the aerodynamic diameter, $d_a$, is the diameter of a unit density sphere with the same settling velocity as the particle as noted previously.

Obtaining a solution of Equation 13 for $v_{dep-c}$, is within the purview of one skilled in the art (see Shimada et al., "Influence of particle inertia on aerosol deposition in a stined turbulent flow field," *J. Aerosol Sci.* Vol. 20, pp. 419–429 (1989); Schneider et al., "A semiempirical model for particle deposition onto facial skin and eyes. Role of air current and electric fields," *J. Aerosol Sci.* Vol. 25, pp. 583–593 (1994); Wood, "A simple method for the calculation of turbulent deposition to smooth and rough surfaces," *J. Aerosol Sci.* Vol. 12, pp. 275–290 (1981); and Sehmel, "Particle deposition from turbulent air flow," *J. Geophys. Res.* Vol. 75, pp. 1766–1781 (1970)). A solution for $V_{dep-c}$ which may be used for $v_{amb}$ in Equation 3 is given by $$v_{amb} = -\frac{v_t}{[(1 - 0.67\tau^{0.49}u_*^{-0.02}v^{-0.49}v_t)e^{-v_t I}] - 1} \quad (14)$$

where $$I = \frac{1}{u_* \left( \frac{3\sqrt{3}}{29\pi} Sc^{-2/3} + 6.2 \times 10^{-4} (\tau^+)^2 \right)} \quad (15)$$

In Equation 15, Sc is the Schmidt number (Sc=v/D), $\tau^+$= (τu$^{*2}$/v), u* is the friction velocity given by Equation 16 below, and the surface is assumed to be smooth.

The friction velocity, u*, may be estimated with the expression $$u_* = \frac{u}{\ln\left(\frac{z}{z_0}\right)} \quad (16)$$

where u is the wind speed at height z above the ground and $z_0$ is the surface roughness. Various authors have compiled values for $z_0$ corresponding to different surfaces. Such information may be found, for example, in the article by Sehmel entitled "Particle and gas dry deposition: a review" (*Atmospheric Environment* Vol. 14, pp. 983–1011, 1980) and in the article by McRae et al. entitled "Development of a second-generation mathematical model for urban air pollution—I" (*Atmospheric Environment* Vol. 16, pp. 679–696, 1982). The value of u can be estimated by consulting data relevant to the given indoor, workplace, or ambient environment. Depending on the sampling application, these data may include previous measurements conducted at the site, literature results for a similar environment, or public-access meteorological data.

When u*<0.4 m/s and $d_a$>0.5 μm, an important simplification to Equation 14 can be made. Specifically, the ambient deposition velocity is largely independent of u*, and $v_{amb}$ may be approximated by $$v_{amb} \approx v_t = \tau g \quad (17)$$

where τ=($\rho_0 d_a^2 C_c$)/(18$\mu$) as noted previously. The simplification can be assumed to hold for all $d_a$ when calculating PM2.5 and PM10, since these mass metrics usually will be dominated by particles with $d_a$>0.5 μm.

Equation 17 can be used to approximate Equation 14 in many cases. In U.S. outdoor environments, u=4 m/s (at z=10 m) is a representative wind speed. Using this wind speed and Equation 16, one finds that u*<0.44 m/s over all surfaces with $z_0$<2.6 cm. This $z_0$-range corresponds to non-urban and non-tree-covered areas. In indoor environments, typical wind speeds are much lower, on the order of u=0.1 m/s. Thus, Equation 17 should be applicable in some outdoor and most indoor sampling applications.

Either Equation 17 or Equation 14 may be used to provide an expression for $v_{amb}$ for use in Equation 3, which provides the expression for the average airborne mass concentration of particles, C. In either case, the expression for $v_{amb}$ is an analytical function whereas the expression for F in equation 3 (the measured particle mass flux distribution) is a discrete function with size bins of a specified number and width. Thus, the expression for $v_{amb}$ must be specified at values of aerodynamic diameter, $d_a$, consistent with the positions of the size bins specified in F.

To evaluate $v_{amb}$ using either Equation 14 and or Equation 17, the variable $\tau=(\rho_0 d_a^2 C_c)/(18\mu)$ should, therefore, be evaluated in a manner consistent with the discrete nature of F. To evaluate $\tau$ corresponding to each size bin, the second-moment average, $\bar{d}_a$, can be used, where $$\bar{d}_a = \left[ \frac{(d_a)_{i,h}^3 - (d_a)_{i,L}^3}{3((d_a)_{i,h} - (d_a)_{i,L})} \right]^{\frac{1}{2}} \quad (18)$$

and $(d_a)_{i,L}$ and $(d_a)_{i,h}$ are the lower and upper limits of size bin i. Alternatively, the value of $d_a$ corresponding to the center of each size bin in F may be used in the expression for $\tau$, but use of the second moment average, $\bar{d}_a$, provides more accurate results.

In addition, $\tau$ depends upon $C_c$, which itself is a function of particle size, and the value of $C_c$ should, therefore, be evaluated in a manner consistent with the discrete nature of F. To calculate $\tau$, $C_c$ is evaluated using $\bar{d}_a$ as expressed in Equation 18.

Further, if Equation 14 for $v_{amb}$ is used, the value of Sc, which depends on $d_{es}$, should also be evaluated in a manner consistent with the discrete nature of F (where Sc=v/D; D=kTC$_c$/3$\pi$ $\mu d_{es}$). Equation 5 is used to calculate $d_{es}$ by using the $d_{pa}$ value corresponding to the midpoint of each size bin in F. In this manner, an expression for $v_{amb}$ may be specified in a way that is consistent with the discrete nature of F for use in Equation 3 for determining the average airborne mass concentration of particles, C.

D. Calibration of the Sampler—Determination of $\gamma_m$

To utilize the passive aerosol sampler according to the present invention in the measurement of unknown particle aerosols, the mesh factor, $\gamma_m$, must be determined. In other words, the passive aerosol sampler must be calibrated. It should be understood that each individual sampler of a specific design does not need to be experimentally calibrated. Rather, one sampler of a given design may be calibrated within a range of wind and turbulence conditions to provide an expression for $\gamma_m$ representative of all samplers of that design under those conditions. The preferred method of calibration for the passive sampler according to the present invention will now be described.

The sampler calibration is preferably carried out using a particle aerosol generated in a wind tunnel for which a reference sampler provides the "known" average airborne mass concentration of particles, C. In short, a passive aerosol sampler according to the present invention is placed in the wind tunnel to collect particles while the reference sampler also collects particles. An experimental expression for F is then determined using microscopy and image analysis for the particle sample collected with the passive aerosol sampler as described above. An empirical expression for $\gamma_m$ is then determined by fitting the size distribution results of the passive sampler to those of the active, mass-based reference sampler as described in detail below.

Figure 5:
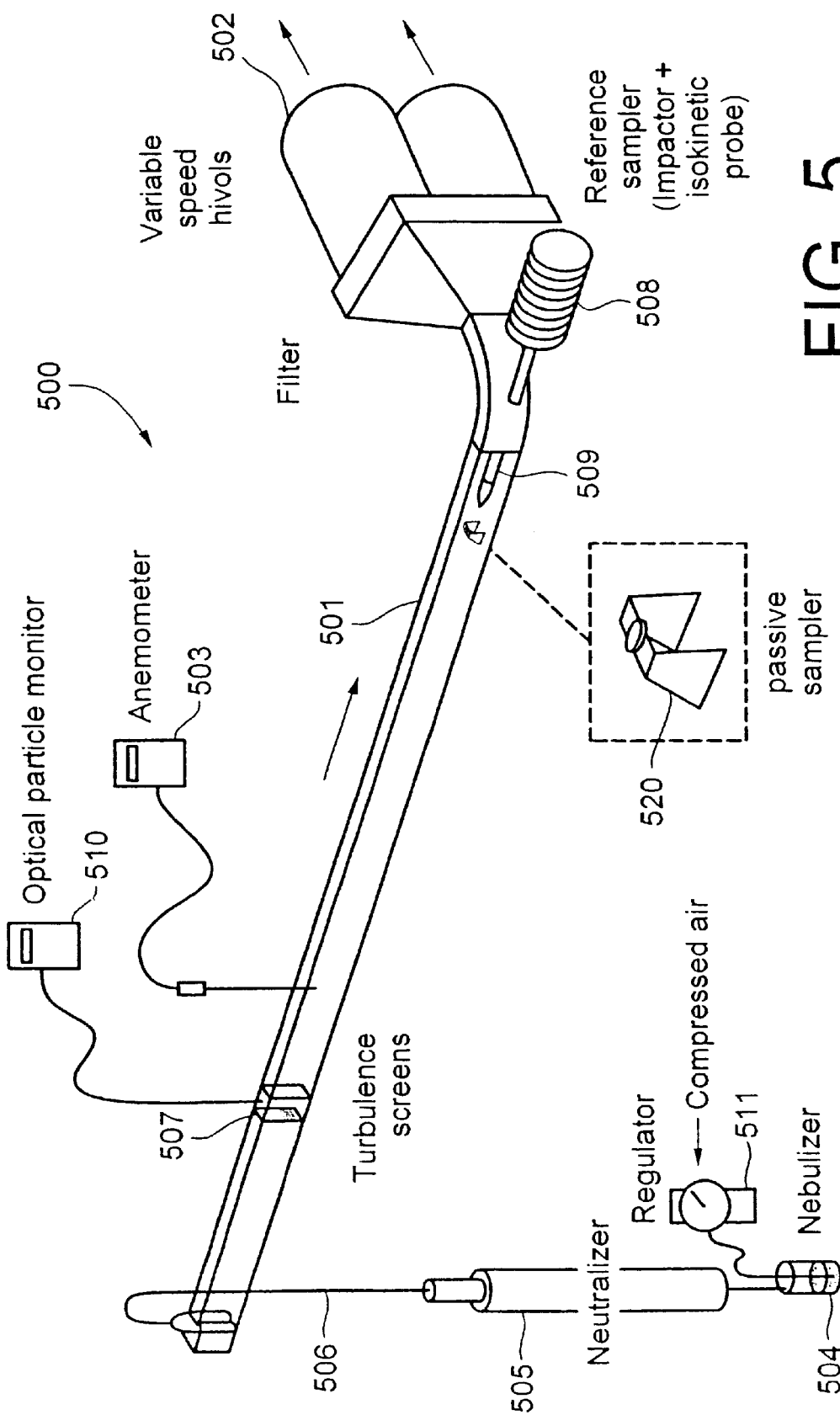

A schematic illustration of a wind tunnel apparatus 500 useful for sampler calibration is shown in perspective view in FIG. 5. The apparatus 500 comprises a wind tunnel 501 with a rectangular cross section of approximately 50 mm by 100 mm and a length of approximately 2.4 m. One end of the wind tunnel 501 is connected, via a 90-degree bend, to two high-volume pumps (hivols) 502 arranged in parallel for pulling air through the wind tunnel 501. Wind speeds in the tunnel 501 may be adjusted using variable transformers (not shown) connected to the hivols 502. A hot-film anemometer 503 (such as Velocicheck Model 8830, TSI Inc., St. Paul, Minn.) may be used to monitor wind speed.

The apparatus 500 further comprises a high-output nebulizer 504 (such as a HEART nebulizer, Westmed, Inc., Tuscon, Ariz.) for continuously dispersing a slurry of distilled water and manufactured dust (such as $SiO_2$ dust from CERAC, Milwaukee, Wis.). The apparatus 500 also comprises a neutralizer 505 (such as Kr-85 neutralizer Model 3054, TSI Inc., St. Paul, Minn.) for neutralizing the aerosol immediately downstream of the nebulizer 504. A regulator 511 regulates a supply of compressed air to the nebulizer 504. A connecting tube 506 passes the neutralized aerosol from the neutralizer 505 to the entrance of the wind tunnel 501. In addition, the apparatus 500 may include a real-time optical particle monitor 510 for qualitatively monitoring aerosol concentration. Turbulence screens 507 may be provided downstream from the entrance of the tunnel 501 to enhance particle mixing in the tunnel 501.

The apparatus 500 further comprises a reference sampler 508 such as an eight-stage Andersen cascade impactor (Andersen Instruments Inc., Smyrna, Ga.) with a 10 mm preseparator and size cuts between 0.43 mm and 9 mm. To minimize particle bounce, a 77 mm polycarbonate membrane substrate with 5.0 mm pore size formed from Isopore filters (Millipore, Bedford, Mass.) may be placed on each impactor stage and saturated with 20 $\mu$L oleic acid. The reference sampler (impactor) 508 is equipped with a probe 509 mounted isoaxially with the wind tunnel 501 flow. Interchangeable probe inlets (not shown) are provided to sample isokinetically at each wind speed. Both the reference sampler (impactor) 508 and probe 509 are preferably electrically grounded.

The wind tunnel apparatus 500 described above is meant to be illustrative rather than restrictive. Those skilled in the art will appreciate that variations of the wind tunnel apparatus 500 may be used to provide a reference aerosol and reference sampler suitable for carrying out calibration of the passive aerosol sampler.

To ensure a reliable calibration of the passive aerosol sampler, the reference aerosol should be spatially uniform in the sampling region of the wind tunnel 501 where the passive aerosol sampler 520 and the probe 509 of the reference sampler 508 are placed. Spatial uniformity of the aerosol may be verified by carrying out multiple sampling measurements under identical wind tunnel conditions using a real-time measuring device (such as an "Aerosizer" device by TSI, Inc.) placed in different positions within the sampling region. It is preferable that a total particle mass concentration and an average particle size have coefficients of variation of less than 10% across the sampling region.

The friction velocity, u*, which is a measure of wind turbulence, should be evaluated in the sampling region of the wind tunnel 501. One reason for evaluating us is for use in the expression for $v_{amb}$ in Equation 14 for calibration of the sampler. Alternatively, u* should be evaluated to verify that u*<0.4 m/s to reliably use Equation 17 for calibrating the sampler. However, it should be understood that once calibration is accomplished, u* values corresponding to actual sampling conditions for unknown aerosols may be provided by Equation 16 for use in the expression for $v_{amb}$. Another reason to evaluate u* in the sampling region of the wind tunnel is that it may be desirable to include u* as a parameter in the expression chosen for $\gamma_m$.

For a wind tunnel such as that illustrated in FIG. 5, the friction velocity us in the wind tunnel is related to the wind speed u at a distance y from the floor or ceiling of the wind tunnel (and centered laterally in the wind tunnel) according to the equation $$u = u_* \left[ 2.5 \ln \left( \frac{y\, u_*}{v} \right) + 5.5 \right] \quad (19)$$

(see H. Schlichting, *Boundary-layer Theory*, 7$^{th}$ Ed., McGraw-Hill, New York, p. 603, 1979). In Equation 19, u* is assumed to be constant in the sampling region of the wind tunnel. In addition, $v$ is the kinematic viscosity, and y is the vertical distance from the floor of the wind tunnel or from the ceiling of the wind tunnel (in either case y does not exceed H/2, where H is the vertical height of the wind tunnel). Thus, by measuring the wind speed u with a hot-film anemometer at various distances y in the sampling region, the friction velocity us in the sampling region can be determined according to equation 19 by fitting the data obtained for u as a function of y.

To carry out the calibration, a passive sampler 520 according to the present invention is placed in the wind tunnel 501 near the impactor probe 509, and aerosol (such as $SiO_2$ dust) is then injected at the entrance to the tunnel 501. Aerosol particles are then collected by both the passive aerosol sampler 520 and the reference sampler (impactor) 508, and a semi-empirical expression for $\gamma_m$ is then determined by fitting the size distribution results of the passive sampler 520 to those of the reference sampler 508 as described below.

A known (reference) mass concentration of airborne particles, $C_{reference}$, is determined using data from the reference sampler (impactor) 508 in the following manner. First, after particle collection is completed, each of the impactor stages is weighed to determine the collected particle mass for the corresponding size bin. Then, for each size bin, the collected mass is divided by the volume of air drawn through the impactor (the air volume is equal to the pump flow rate multiplied by the sampling time). This provides a known (reference) concentration of airborne particles, $C_{reference}$, as a function of aerodynamic diameter.

The particle count data from the passive aerosol sampler 520 are determined by microscopy and image analysis as described in the section above (Determination of the mass flux distribution F). The particle count distribution for the passive aerosol sampler is specified in discrete size bins corresponding to the discrete size bins of the reference sampler 508. The particle count distribution for particles collected by the passive aerosol sampler may then be converted to a mass flux distribution F using Equation 11 as described above.

A functional form for $\gamma_m$ with fitted parameters may then be chosen, and the concentration of airborne particles for the passive sampler, $C_{passive}$, may be written according to Equation 3 as $$C_{passive} = F/(v_{amb}\gamma_m). \quad (20)$$

The calibration involves varying the fitted parameters of $\gamma_m$ to minimize the difference between $C_{passive}$ and $C_{reference}$.

Generally, the expression chosen for $\gamma_m$ should be a function of both the aerodynamic diameter, $d_a$, and the friction velocity, u*. A preferred general functional form for $\gamma_m$ is given by $$\gamma_m = A\, Re_p^{-B}(\tau^+)^E Sc^G (v_{amb}/u^*)^H \quad (21)$$

where $Re_p = (d_a v_t/v)$, $\tau^+ = [(\rho_0 d_a^2 C_c)/(18\mu)]u^{*2}/v$, $Sc = v/D$, $D = kTC_c/3\pi\mu d_{es}$, and A, B, E, G and H are fitted parameters determined by minimizing the difference between $C_{passive}$ and $C_{reference}$. Though $\gamma_m$ in Equation 21 is given as a product of terms, $\gamma_m$ can also be expressed as a sum comprising combinations of the terms given in Equation 21.

It has been found that an advantageous form for $\gamma_m$ is given by $$\gamma_m = 1, d_a < M\, \mu m\, \gamma_m = A Re_p^{-B}, d_a \geq M\, \mu m \quad (22)$$

where A, B and M are fitted parameters determined by minimizing the difference between $C_{passive}$ and $C_{reference}$.

A preferred method of determining A, B and M in Equation 22 (or the fitted parameters in Equation 21) above is to carry out multiple calibration experiments at different wind speeds in the wind tunnel 501 and to minimize the sum-of-squares difference between $C_{passive}$ and $C_{reference}$ at each size bin, across all experiments. This may be accomplished by defining an optimization parameter, OP, as $$OP = \sum_{j=1}^{J} \left[ \sum_{i=1}^{I} \left( \frac{(dC/d\log d_a)_{passive} - (dC/d\log d_a)_{reference}}{(dC/d\log d_a)_{reference}} \right)_i^2 \right]_j \quad (23)$$

where $(dC/d\log d_a)$ is the particle concentration for size bin i (normalized by the width of the bin), j is the experiment number, J is the total number of calibration experiments, and I is the number of bins. Conventional iterative methods are known in the art for minimizing functions such as that expressed in Equation 23. A particularly convenient method of minimizing OP in Equation 23, thereby determining the fitted parameters A, B and M in Equation 22, involves inputting the particle concentration data into a commercially available software spreadsheet program and utilizing a built-in function minimization tool. An example of such a minimization tool is the "Solver" tool in the Microsoft Excel (Seattle, Wash.) spreadsheet program. Size bins for which either the reference sampler 508 or the passive sampler 520 has zero mass should not be included in the optimization.

As an example, a passive aerosol sampler according to the present invention such as that illustrated in FIG. 1 was calibrated according to the methods disclosed herein. The sampler comprised a body (SEM mount) 12.7 mm in diameter and removable mesh cover 15 mm in diameter. The mesh sheet comprised a mesh such as that illustrated in FIGS. 1b and 2 having a mesh thickness of 127 $\mu$m, a percent open area of about 27%, and apertures of conical cross section (top diameter of 160 $\mu$m; bottom diameter of 225 $\mu$m) with a center-to-center spacing of about 280 $\mu$m. The collection region was approximately 7 mm in diameter and 1.2 mm deep. A commercially available $SiO_2$ dust (CERAC, Milwaukee, Wis.) was used to provide the particle aerosol in the wind tunnel. A wind tunnel like that illustrated in FIG. 5 having a reference sampler comprising an eight-stage Andersen cascade impactor (Andersen Instruments Inc., Smyrna, Ga.) was also used. The reference sampler was configured to provide particle count data in nine size bins.

Using the methods described above and a functional form for $\gamma_m$ like that given in Equation 22, the following expression for $\gamma_m$ was obtained:

$$\gamma_m=1, d_a<1.63 \ \mu m \quad \gamma_m=(5.95\times10^{-3})Re_p^{-0.439}, d_a\geq1.63 \ \mu m \quad (24)$$

where $Re_p=(d_a v_t/v)$. This relatively simple expression contains one dimensionless group and three parameters, including the diameter at which $\gamma_m$ starts to steadily decrease with $d_a$. Note that this expression is not dependent on u*, and therefore does not require estimating us when sampling.

Using expressions for $\gamma_m$ and $v_{amb}$ such as those described herein, Equation 3 may be used to determine the average airborne mass concentration of particles for an unknown aerosol sampled with the passive aerosol sampler according to the present invention as described above.

III. ALTERNATIVE EMBODIMENTS

The passive aerosol sampler according to the present invention has been described in which the body of the sampler comprises an SEM mount. As a result, particle samples collected with the passive aerosol sampler may be conveniently analyzed by SEM to provide images for subsequent image analysis. The techniques of environmental SEM (ESEM), optical microscopy and AFM (if the SEM-mount body is compatible) may also be used to analyze particle samples with this type of sampler. However, it may be desirable to provide a passive aerosol sampler in which the particle samples are collected on sample mounts tailored for transmission electron microscopy (TEM), atomic force microscopy (AFM), or another method of image of image formation. Such alternative embodiments of the passive aerosol sampler are now described.

Figure 6:
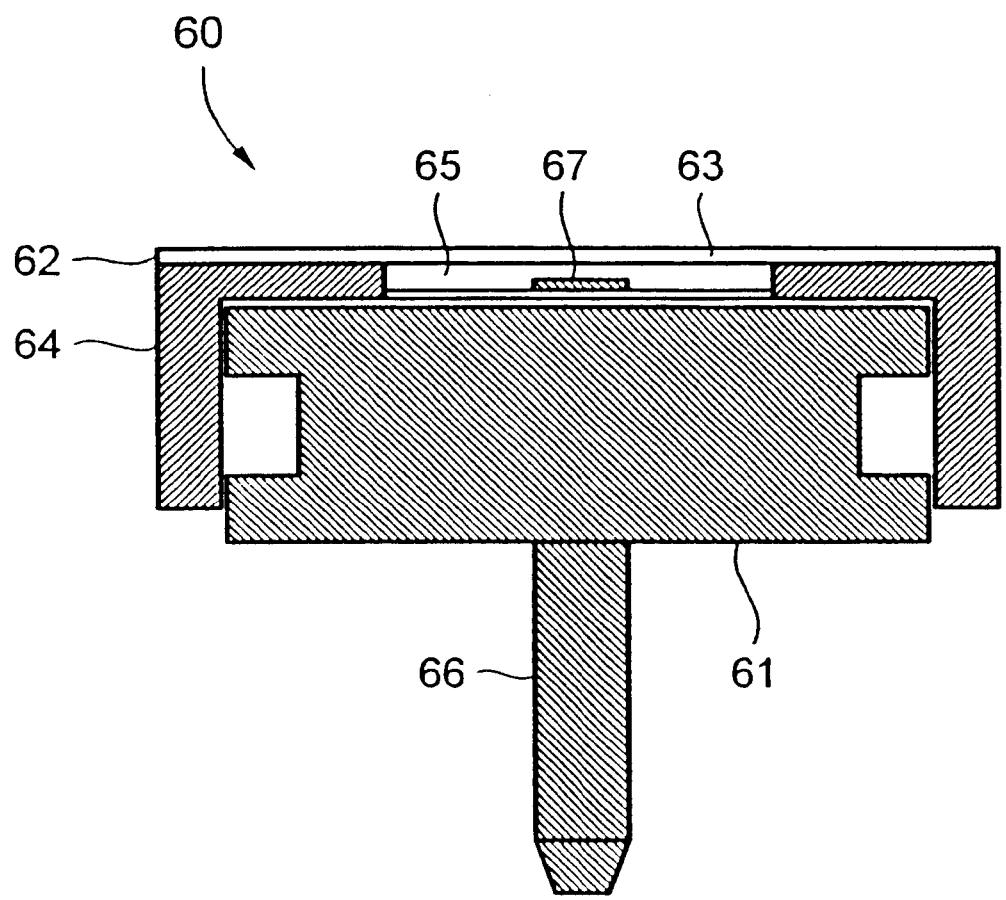

An embodiment of the passive aerosol sampler configured to provide a collected particle sample for analysis by TEM is illustrated in FIG. 6. As illustrated in FIG. 6, the sampler 60 comprises a body (SEM mount) 61 upon which is disposed a conventional 3 mm TEM grid 67 having a thin, electrically conducting support film (not shown) on the upper grid surface. The TEM grid 67 is disposed at a central portion of the upper surface of the body 61. A removable mesh cover 62 comprising a mesh sheet 63 securely bonded to spacer ring 64 is positioned such that the mesh sheet 63 is disposed above the TEM grid 67. A semi-quiescent collection region 65 is formed between the mesh sheet 63 and the upper surface of the body 61. Though the sampler 60 is illustrated with a body 61 having a protruding post 66, the body 61 may alternatively be provided with a threaded mounting hole as noted previously. In this embodiment, the thin, electrically conducting film at the upper surface of the TEM grid forms the particle collection surface.

The sampler 60 is cleaned and assembled in substantially the same manner as that for the sampler 10 illustrated in FIG. 1a, except that a small amount of spray mount adhesive is applied to the central portion of the upper surface of the body 61 to hold the TEM grid 67 in place. Generally, the TEM grid 67 is positioned with the thin, electrically conducting support film arranged at the upper grid surface rather than at the lower grid surface to prevent damage to the support film.

Figure 3B:
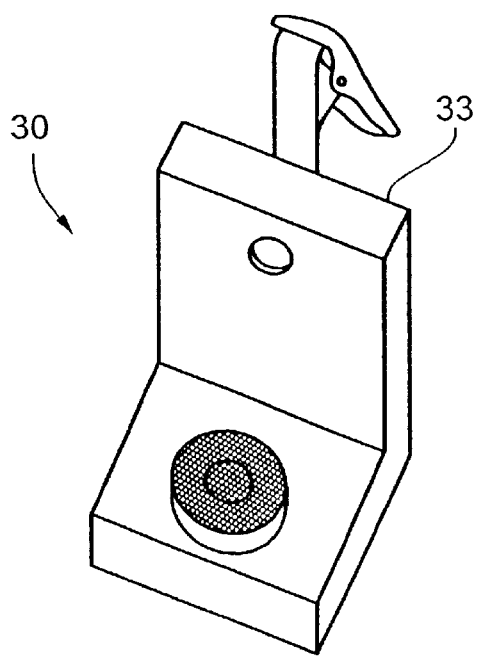

An advantage of configuring the TEM grid 67 with a conventional SEM-mount body 61 as illustrated in FIG. 6 is that special bodies and holders are not required for such an embodiment. Holders such as holders 33 and 43 illustrated in FIGS. 3 and 4 may be utilized. Alternatively, a holder having a protruding, threaded screw rather than a mounting hole as described previously may also be used.

The deployment and calibration for the sampler 60 illustrated in FIG. 6 is substantially the same as that previously described for the sampler 10 illustrated in FIG. 1a. The analysis of the collected particle sample differs from that previously described, however, because TEM rather than SEM is used to obtain images of the collected particles. In addition, the collected particle sample may be analyzed by EDXRF to determine the chemical constituents of the collected particles. Further, analysis by TEM provides the potential to analyze the collected particle sample using electron energy loss spectrometry (EELS) to gain additional chemical and bonding information about the collected particles.

Figure 7:
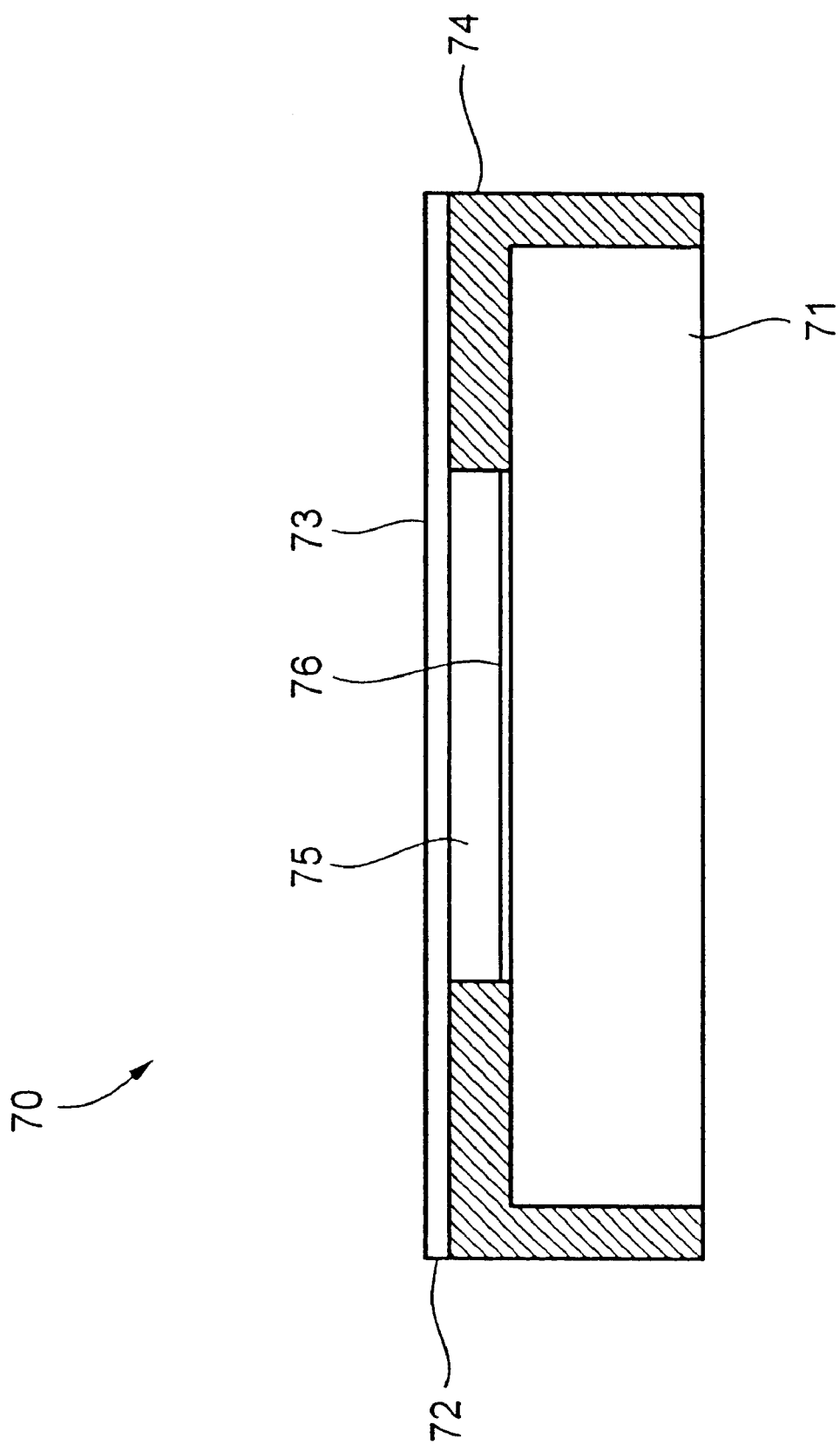

An embodiment of the passive aerosol sampler configured with a body comprising a conventional AFM sample mount is illustrated in FIG. 7. As illustrated in FIG. 7, the sampler 70 comprises a body 71 in the form of a conventional disk-shaped AFM sample mount. A removable mesh cover 72 comprising a mesh sheet 73 securely bonded to a spacer ring 74 is attached to the body 71 with removable spray mount adhesive. A smooth collection surface 76 is provided at the base of a collection region 75 in a manner such as that previously described for embodiments based on SEM sample mounts. The body 71 is mounted on a holder (not shown) using double-sided adhesive tape or other conventional removable adhesives. The holder may be provided in a configuration for personal exposure monitoring, such as holder 33 illustrated in FIGS. 3a and 3b, or in a configuration for stationary exposure monitoring, such as holder 43 illustrated in FIG. 4. Conventional AFM sample mounts about 9.9 mm to 15 mm in diameter and about 1 mm to a few mm in height formed of aluminum or other metals or alloys are advantageous, but AFM sample mounts in other configurations may be used. Because conventional AFM sample mounts are typically thinner than conventional SEM sample mounts, the spacer ring 74 may extend to the base of the body 71 as illustrated in FIG. 7.

The deployment and calibration for the sampler 70 illustrated in FIG. 7 is substantially the same as that previously described for the sampler 10 illustrated in FIG. 1a. The analysis of the collected particle sample differs from that previously described, however, because AFM rather than SEM is used to obtain images of the collected particles. The use of AFM, however, allows the possibility of obtaining high resolution images without placing the collected particle sample in a vacuum.

The instant invention has been described with respect to particular preferred embodiments. The invention to be protected, however, is intended to be defined by the literal language of the claims and the equivalents thereof.

We claim:

1. A passive aerosol sampler, comprising:
    a body provided with an electrically conducting collection surface; and
    a removable mesh cover, the removable mesh cover comprising a mesh sheet having a plurality of apertures therein, wherein a first portion of the removable mesh cover is removably attached to the body and a second portion of the removable mesh cover is disposed adjacent to the collection surface, wherein aerosol particles can deposit through the apertures onto the collection surface.

2. The passive aerosol sampler of claim 1, wherein the first portion of the removable mesh cover comprises a circumferential portion of the removable mesh cover.

3. The passive aerosol sampler of claim 2, wherein the body is configured as a sample mounting member for use in microscopy.

4. The passive aerosol sampler of claim 3, further comprising a holder that holds the body, wherein the holder is configured for use in personal exposure monitoring.

5. The passive aerosol sampler of claim 3, further comprising a holder that holds the body, wherein the holder is configured for use in stationary exposure monitoring.

6. The passive aerosol sampler of claim 3, wherein the plurality of apertures of the mesh sheet are arranged in a predetermined pattern.

7. The passive aerosol sampler of claim 6, wherein the predetermined pattern is a triangular-lattice pattern.

8. The passive aerosol sampler of claim 6, wherein the mesh sheet has a percent open area ranging from 9 percent to 38 percent.

9. The passive aerosol sampler of claim 6, wherein the apertures are circular in shape and have diameters ranging from 75 micrometers to 610 micrometers.

10. The passive aerosol sampler of claim 6, wherein each aperture has a first opening with a first diameter and a second opening with a second diameter, the second diameter being greater than the first diameter, and wherein the apertures are configured such that the second openings are disposed closer to the collection surface than are the first openings.

11. The passive aerosol sampler of claim 3, wherein the sample mounting member comprises a scanning electron microscopy sample mount.

12. The passive aerosol sampler of claim 11, wherein the first portion of the removable mesh cover further comprises a circumferential spacer attached to the mesh sheet.

13. The passive aerosol sampler of claim 12, wherein the body is formed from one of aluminum and carbon.

14. The passive aerosol sampler of claim 12, wherein the collection surface comprises smooth, metal adhesive tape disposed on the body.

15. The passive aerosol sampler of claim 14, wherein the metal adhesive tape comprises aluminum.

16. The passive aerosol sampler of claim 11, wherein the body is circular in shape and ranges from about 10 mm to 32 mm in diameter, the collection surface is circular in shape and ranges from about 5 mm to 17 mm in diameter, and a distance between the collection surface and the second portion of the removable mesh cover ranges from about 1 mm to 3 mm.

17. The passive aerosol sampler of claim 11, wherein the second portion of the removable mesh cover comprises a central portion of the removable mesh cover.

18. The passive aerosol sampler of claim 17, wherein the second portion of the removable mesh cover is disposed parallel to the collection surface.

19. The passive aerosol sampler of claim 3, further comprising a transmission electron microscopy grid disposed on the body, wherein the collection surface comprises a thin, electrically conducting support film disposed on the transmission electron microscopy grid.

20. The passive aerosol sampler of claim 3, wherein the sample mounting member comprises an atomic force microscopy sample mount.

21. A method of determining an average airborne concentration of aerosol particles as a function of particle size in a measurement region from a sample of aerosol particles collected on a collection surface of a passive aerosol sampler, the passive aerosol sampler having a body provided with the collection surface and a removable mesh cover removably attached to the body, the removable mesh cover having a plurality of apertures therein, comprising the steps of:

carrying out microscopy on the sample of aerosol particles collected on the collection surface;

obtaining images of the sample of aerosol particles using said microscopy;

determining a particle-count size distribution using image analysis of the images; and calculating the average airborne concentration of aerosol particles as a function of particle size from the particle-count size distribution using a mathematical model having a theoretical component and an empirical component, wherein the empirical component is related to the geometrical characteristics of the mesh cover.

22. The method of claim 21, wherein said concentration is a mass concentration.

23. The method of claim 22, wherein the mathematical model comprises an equation $C=F/(v_{amb}\gamma_m)$, wherein $C$ is the average airborne mass concentration of aerosol particles, $F$ is an average mass flux of particles deposited on the collection surface, $v_{amb}$ is an ambient deposition velocity for particles depositing onto a smooth surface, $v_{amb}$ being the theoretical component, and $\gamma_m$ is the empirical component related to the geometrical characteristics of the mesh cover.

24. The method of claim 23, wherein $\gamma_m$ comprises a function of the form $A \cdot Re_p^{-B}$, wherein A and B are fitted parameters determined through a calibration process, $R_{ep}=(d_a v_t/v)$, $v_t=(g\rho_0 d_a^2 C_c)/(18\mu)$, $$C_c = 1 + \left(\frac{2L}{d_{ev}}\right)\left(1.257 + 0.4 e^{-\left(\frac{1.1 d_{ev}}{2L}\right)}\right),$$

$d_{ev}=d_{pa}/S_v$, $d_{pa}$=the projected area diameter of a measured particle, $S_v$ is the volume shape factor, $d_a$ is the aerodynamic diameter, $\rho_0$ is the unit particle density, $v$ is the kinematic viscosity, $\mu$ is the dynamic viscosity, g is the gravitational acceleration, and L is the mean free path for air.

25. The method of claim 23, wherein $v_{amb}$ is given by the expression $v_{amb}=v_t=(g\rho_0 d_a^2 C_c)/(18\mu)$, wherein $$C_c = 1 + \left(\frac{2L}{d_{ev}}\right)\left(1.257 + 0.4 e^{-\left(\frac{1.1 d_{ev}}{2L}\right)}\right),$$

$d_{ev}=d_{pa}/S_v$, $d_{pa}$=the projected area diameter of a measured particle, $S_v$ is the volume shape factor, $d_a$ is the aerodynamic diameter, $\rho_0$ is the unit particle density, $\mu$ is the dynamic viscosity, g is the gravitational acceleration, and L is the mean free path for air.

26. The method of claim 21, wherein the collection surface is a thin film disposed on a surface of a transmission electron microscopy grid provided on the body and wherein the microscopy is transmission electron microscopy.

27. The method of claim 21, wherein the microscopy is atomic force microscopy.

28. The method of claim 21, wherein the microscopy is environmental scanning electron microscopy.

29. The method of claim 21, wherein the microscopy is optical microscopy.

30. The method of claim 21, wherein the microscopy is scanning electron microscopy.

31. The method of claim 21, wherein the empirical component is determined through calibration with a reference aerosol.

32. The method of claim 21, wherein the collection surface is an electrically conducting collection surface.

33. The method of claim 21, wherein the empirical component is a function of the aerodynamic diameter, $d_a$, and the friction velocity, $u^*$.

34. The method of claim 33, wherein the empirical component further comprises at least two fitted parameters whose values are determined through calibration with a reference aerosol.

* * * * *

UNITED STATES PATENT AND TRADEMARK OFFICE
CERTIFICATE OF CORRECTION

PATENT NO. : 6,321,608 B1  Page 1 of 1
DATED : November 27, 2001
INVENTOR(S) : Jeff Wagner et al.

It is certified that error appears in the above-identified patent and that said Letters Patent is hereby corrected as shown below:

Column 1,
Lines 4-6, replace with the following:

-- At least some aspects of this invention were made with Government support under contract or grant nos. P200A40274-96, ES07018, OH03774, and U-915321-01-0. The Government may have certain rights in the invention. --

Signed and Sealed this

Sixteenth Day of September, 2003

JAMES E. ROGAN
*Director of the United States Patent and Trademark Office*